(12) United States Patent
Hospodor

(10) Patent No.: US 12,076,308 B2
(45) Date of Patent: Sep. 3, 2024

(54) TERPENE CONTROL IN SCALEABLE CANNABINOID MEDICINAL FORMULATIONS

(71) Applicant: Andrew Hospodor, Santa Cruz, CA (US)

(72) Inventor: Andrew Hospodor, Santa Cruz, CA (US)

( * ) Notice: Subject to any disclaimer, the term of this patent is extended or adjusted under 35 U.S.C. 154(b) by 727 days.

(21) Appl. No.: 17/063,068

(22) Filed: Oct. 5, 2020

(65) Prior Publication Data

US 2021/0085638 A1 Mar. 25, 2021

Related U.S. Application Data

(63) Continuation of application No. 15/351,399, filed on Nov. 14, 2016, now abandoned, which is a continuation-in-part of application No. 14/714,222, filed on May 15, 2015, now abandoned.

(51) Int. Cl.
| | |
|---|---|
| *A61K 31/352* | (2006.01) |
| *A61K 36/185* | (2006.01) |
| *A61K 45/06* | (2006.01) |
| *A61K 31/01* | (2006.01) |
| *A61K 31/015* | (2006.01) |
| *A61K 31/05* | (2006.01) |

(52) U.S. Cl.
CPC .......... *A61K 31/352* (2013.01); *A61K 36/185* (2013.01); *A61K 45/06* (2013.01); *A61K 31/01* (2013.01); *A61K 31/015* (2013.01); *A61K 31/05* (2013.01)

(58) Field of Classification Search
CPC .... A61K 31/658; A61K 31/01; A61K 31/352; A61P 35/00
See application file for complete search history.

(56) References Cited

FOREIGN PATENT DOCUMENTS

| WO | WO-9420080 A1 * | 9/1994 | ............. A61K 31/01 |
| WO | WO-2009147438 A1 * | 12/2009 | ........... A61K 31/138 |

OTHER PUBLICATIONS

Golub et al., Science, vol. 286, Oct. 15, 1999, pp. 531-537.*
Grotenhermen, F, Clinical Pharocokinet., 2003, vol. 42, No. 4, pp. 327-360.*
Wu et al. Nat. Genet., May 2014, vol. 46, No. 5, pp. 444-450.*
Zerrifi et al. Toxins, 2020, vol. 527, No. 12, pp. 1-20.*
Hurov et al. Annu. Rev. Med., 2014, vol. 65, pp. 157-170.*

* cited by examiner

*Primary Examiner* — San Ming R Hui
(74) *Attorney, Agent, or Firm* — Robert J. Rapp

(57) ABSTRACT

The present invention administers a cannabinoid medication to a patient followed by observing one or more physiological responses in the patient during a first period of time when treating a medical condition. The cannabinoid medication may include one or more specific types of cannabinoids at a dosage level or may include a plurality of discrete formulations where each formulation includes masses of specific cannabinoids that may be used for treating one or more ailments.

20 Claims, 3 Drawing Sheets

TERPENE CONTROL IN SCALEABLE CANNABINOID MEDICINAL FORMULATIONS

CROSS REFERENCE TO RELATED APPLICATIONS

This application is a continuation and claims priority benefit of U.S. patent application Ser. No. 15/351,399, filed Nov. 14, 2016, entitled. Terpene Control in Scaleable Cannabinoid Medicinal Formulations, which is a continuation in part and claims priority benefit of U.S. patent application Ser. No. 14/714,422, filed May 15, 2015 entitled Scaleable Cannabinoid Treatment Regimen and Medicinal formulations, the disclosures of which are incorporated herein by reference.

BACKGROUND OF THE INVENTION

Field of the Invention

The presently claimed invention relates to treating various ailments. More specifically the presently claimed invention relates to the administration of cannabinoids as a medicinal treatment to a patient.

Descriptions of the Related Art

Many medical schools teach that that metastases are clonal of a primary tumor. However, aggressive adenocarcinoma type cancers appear to constantly mutate due to miss-correction of the DNA. Pancreatic cancer is one of the deadliest forms of adeno-carcinoma, with patient survival measured in months. When treating pancreatic cancer, doctors expect chemotherapy agents to quell metastases, and this is simply not correct. Although they can originate from the primary tumor, metastases may be very different from the primary tumor. Furthermore, the pancreatic primary tumor rarely kills the host. Instead, metastases of the cancer interfere with other endocrine organs, the intestinal tract and even the lungs. Certain forms of cancer overexpress numerous cannabinoid receptors, and Donadelli reported that the CannabinoidReceptor1 (CB1) ligand Rimonabant (SR141716, e.g. "SR1") shrunk pancreatic cancer cells in mice. Adenocarcinoma cells are known to have many CB1 receptors, and THC is known to bind to CB1 receptors (i.e. THC is a CB1 ligand). Donadelli also discusses that cannabinoids when combined with Gemcitabine acts as autophagy and induce apoptosis in pancreatic cancer cells.

Chemotherapy is a known treatment regimen used to treat cancer. One commonly used chemotherapy agent is Gemcitabine. "Gemcitabine is a member of a group of chemotherapy drugs known as anti-metabolites. It prevents cells from making DNA, which stops cell growth and causes the cells to die." (Quote from cancer.org). Antimetabolites are very similar to normal substances within the cell, when cells incorporate an antimetabolite into their cellular metabolism, the cells cannot function properly and are unable to divide. Since antimetabolites are cell-cycle specific they attack cells at very specific phases in their life cycle. Antimetabolites are classified according to the substances with which they interfere, i.e. they are antagonize or inhibit folic acid, pyrimidine, purine, and adenosine deaminase. Examples include: Folic acid antagonist: Methotrexate|Pyrimidine antagonist: 5-Fluorouracil, Foxuridine, Cytarabine, Capecitabine, and Gemzar|Purine antagonist: 6-Mercaptopurine and 6-Thioguanine|Adenosine deaminase inhibitor: Cladribine, Fludarabine and Pentostatin.

Antimetabolites, like many chemotherapy agents are toxic to all cells, not just cancer cells. Because cancer cells grow much faster than normal cells, they are disproportionately affected by the chemotherapy.

A proposed method to treat adenocarcinoma involves administering a substance that interferes with a Kirsten RAt Sarcoma oncogene homolog (i.e. a KRAS inhibitor) from the mammalian ras gene family. The KRAS gene is known to produce a protein that is commonly referred to as K-Ras that accelerates tumor growth. Mutations in the KRAS gene can result in normal cells dividing uncontrollably with an increased probability of turning cancerous. Recently a KRAS inhibitor was identified as the molecule SML-8-73-1 by the University of Texas Southwester Cancer Research Center.

Currently, physicians cannot prescribe and medical cannabis dispensaries do not offer cannabinoid medications that span a range of formulations. Because of this a patient cannot currently be provided with cannabinoid based medications according to a treatment regimen where the dosage of specific cannabinoids may be easily varied over time. Formulations of cannabinoid based medications that span a range of cannabinoid dosages are easily be administered to a patient as promising new treatments for cancer or other ailments that may. Such treatment are desperately needed.

Human patents administered high dosage levels of THC, such as Marino or Drobinol, often experience psychoactive side effects of the drug to an extent that may cause the patient to avoid the medication. Because of this a regimen that mitigates THC while allowing the patient to adjust to side effects of the cannabinoid is needed.

Conventional cancer treatments do not attack cancer using multiple pathways. What is needed is a regimen that treats cancer by attacking cancer in a plurality of different ways. Such a treatment could exploit the pathways associated with CB1 ligands, Antimetabolites and KRAS.

Cannabinoids also show promise for treating both ailments and side effects. Marinol and Dronobinol are medications that include THC that are used to treat the side effects of chemotherapy. Patients sometimes stop taking Marinol or Dronobinol in instances when they don't like to psychoactive effects of THC. This is a very significant drawback of Marinol and Dronobinol: a patient cannot gain benefit from a medication when they don't take it.

Because of the federal prohibition of cannabis, the effect of cannabinoids on people has not been systematically studied by medical science for nearly 100 years. What are needed are formulations of cannabinoids with different milligram dosages of one or more cannabinoids such that the effect of different individual and combined cannabinoids can be studied. What are also needed are the identification of new effective treatment regimens for treating ailments and side effects.

SUMMARY OF THE PRESENTLY CLAIMED INVENTION

Embodiments of the presently claimed invention include a formulation of matter that include one or more cannabinoids that have a mass that corresponds to a cannabinoid dosage profile distributed in a volume of the formulation and one or more terpenes. Each of the one or more terpenes may be distributed in the volume of the formulation and have a mass corresponding to a terpene dosage profile, at least a portion of at least one of the one of the one or more terpenes was derived from a non-cannabinoid containing source, and the portion of the at least one terpene of the one or more terpenes may have been combined with the one or more cannabinoids such that the formulation includes a mass of the at least one terpenes distributed in the volume of the formulation are according to the terpene dosage profile.

The presently claimed invention also relates to a plurality of discrete cannabinoid formulations, where a mass of at least one cannabinoid of three of more cannabinoid types change at least according to an exponential function in a series of steps, where each of the discrete cannabinoid formulations are included in at least one of a pill, a capsule, a suppository, or a tincture.

DETAILED DESCRIPTION

An embodiment of the presently claimed invention administers a cannabinoid medication to a patient followed by observing one or more physiological responses in the patient during a first period of time. The cannabinoid medication may include one or more specific types of cannabinoids at an initial dosage level. In certain instances the cannabinoid dosage level is incremented over the first period of time. The dose of a cannabinoid corresponds to a mass, in milligrams, of one or more cannabinoid types administered to the patient over a period of time, typically over a day. When treating cancer, the cannabinoid treatment may be combined with one or more other methods for treating cancer, such as, administering a chemotherapy agent, a KRAS inhibitor, or both. When treating other ailments, a practitioner may select a cannabinoid formulation from a plurality of cannabinoid medications according to a treatment regime. The practitioner may also select from a variety of dosage levels in milligrams of cannabinoids per kilogram of body mass (mg/Kg).

The present disclosure relates to formulations and methods for fabricating cannabinoid containing medicinal formulations where laboratory tested cannabinoid containing intermediate products are combined according to formations that create dosages of cannabinoids in a unit volume of one or more formulations.

The present invention for treating cancer attacks cancer in several different ways, such as: 1. Trigger autophagy/apoptosis in cancer cells through a Reactive Oxygen Species (ROS) mediated mechanism using cannabinoids; 2. Modulate DNA mis-repair with an antimetabolite chemotherapy agent; 3. Slow the grow Suppress the KRAS gene with a KRAS inhibitor; 4. Target mutant antigens with checkpoint blockade immunotherapy. Donadelli has already demonstrated 1 in Italy by reducing pancreatic cancer tumors in mice after administering high dosages of CB1 ligands such as SR1. Donadelli, however, never adapted this treatment for humans, never combined tetrahydrocannabinol (THC) with cannabidiol (CBD), never considered treating cancer with a KRAS inhibitor or with a checkpoint blockade immunotherapy. Checkpoint blockade immunotherapy is discussed by D. R. Leach, et al in a document entitled: "Enhancement of Antitumor Immunity by CTLA-4 Blockade," Science, 22 Mar. 1996.

Figure 1:
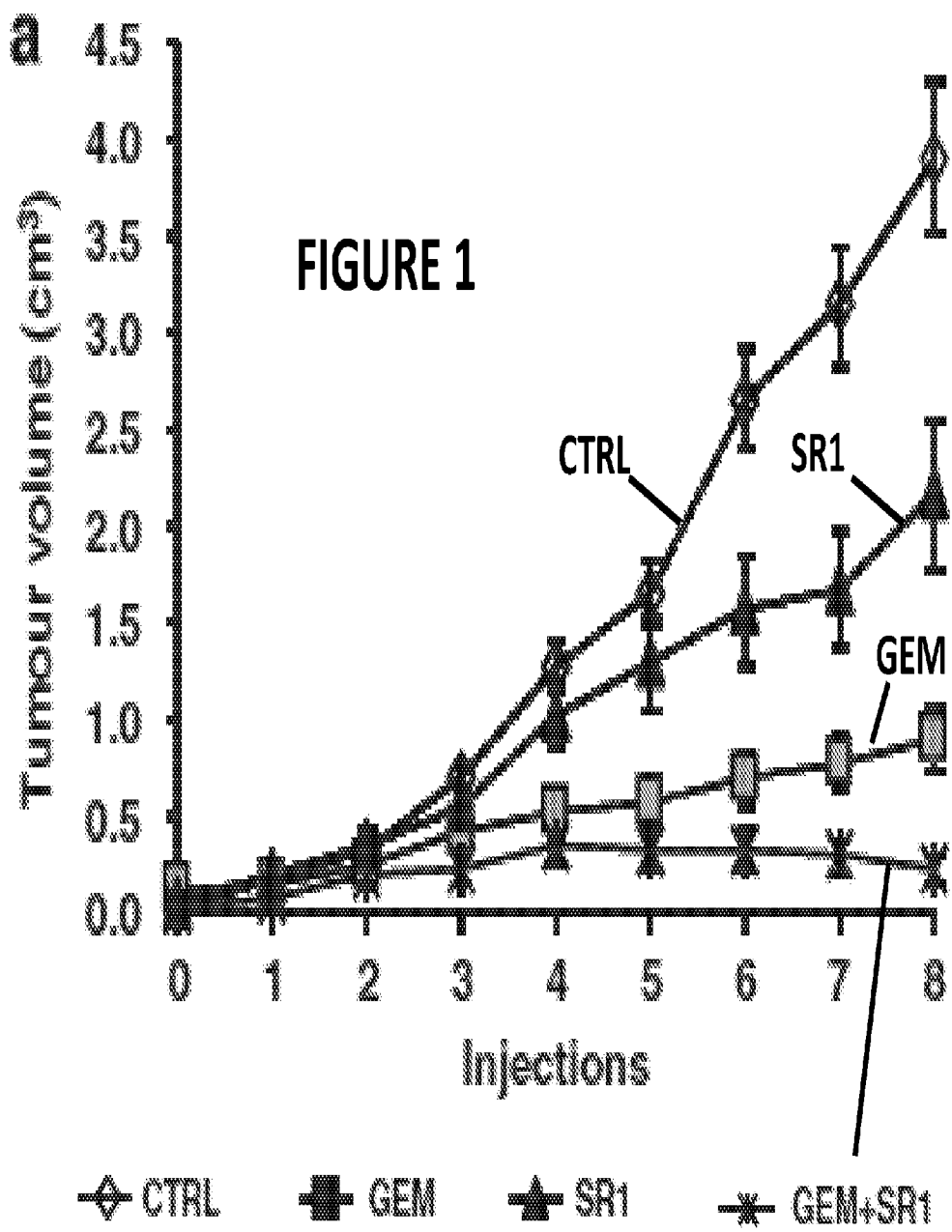
FIG. 1 illustrates a graph of data observed by Donadelli when treating pancreatic cancer in mice.

FIG. 1 illustrates a graph of data observed by Donadelli when treating pancreatic cancer in mice. FIG. 1 includes four separate experiments where the volumes of tumors were measured over time while administering medications according to four different treatment regimens. In a first experiment a control group received no medication. Note that tumor volume increased most dramatically in the control group curve CRTL. Note also that when CB1 ligand SR1 was administered in a number of injections the tumor volume grew at a slower rate in the SR1 curve as compared to the control group curve CRTL. FIG. 1 also shows that when Gemcitabine (GEM) was injected over time, tumor volume grew at even a slower rate as indicated by the GEM curve including lower tumor volumes than the SR1 curve. Notice also that while the rate of growth of pancreatic cancer was slowed when SR1 or Gemcitabine were administered to the mice, the volume of the cancer tumors continued to increase throughout the experiment in the SR1 and in the GEM curves. The fourth curve GEM+SR1 in FIG. 1 illustrates data taken by Donadelli when both the SR1 CB1 ligand and Gemcitabine were combined. In the GEM+SR1 curve the tumor volume peaked by the fourth injection. The GEM+SR1 curve also shows that tumor volume was markedly reduced by the eighth injection.

Embodiments of the present invention may first administer an initial cannabinoid dosage to a patient while one or more physiological effects of the cannabinoid may be monitored. The present invention may also increase the dosage of cannabinoids over time while monitoring one or more pathological factors until a pathological effect has been observed.

The one or more physiological effects may also be monitored over the course of treatment. In the instance where a physiological effect that was initially observed is determined to no longer be observed or is observed at a reduced level after a cannabinoid administration, a determination may be made that the patient's body is adapting to the presence of the cannabinoids.

Subsequently, a practitioner may identify that a patient may have stopped taking the cannabinoid medication when a physiological effect is once again observed after the patient consumes a cannabinoid medication. In the instance where a practitioner identifies that a patent may have stopped taking the cannabinoid medication, the practitioner may have the patient watched more closely. Reasons why a patient may stop taking a medication include: forgetfulness, distractions, and confusion. In certain instances a patient may forget because of their weakened condition, in another instance the patient be distracted by thinking about their condition, or in yet another instance the patient may be confused when they lose track of passing time.

Thus, by monitoring that a cannabinoid related physiological effect was first observed, was subsequently observed to abate, and then was observed to return after cannabinoids were administered may be used to identify that a patient requires additional assistance in maintaining a recommended treatment regimen.

Figure 2:
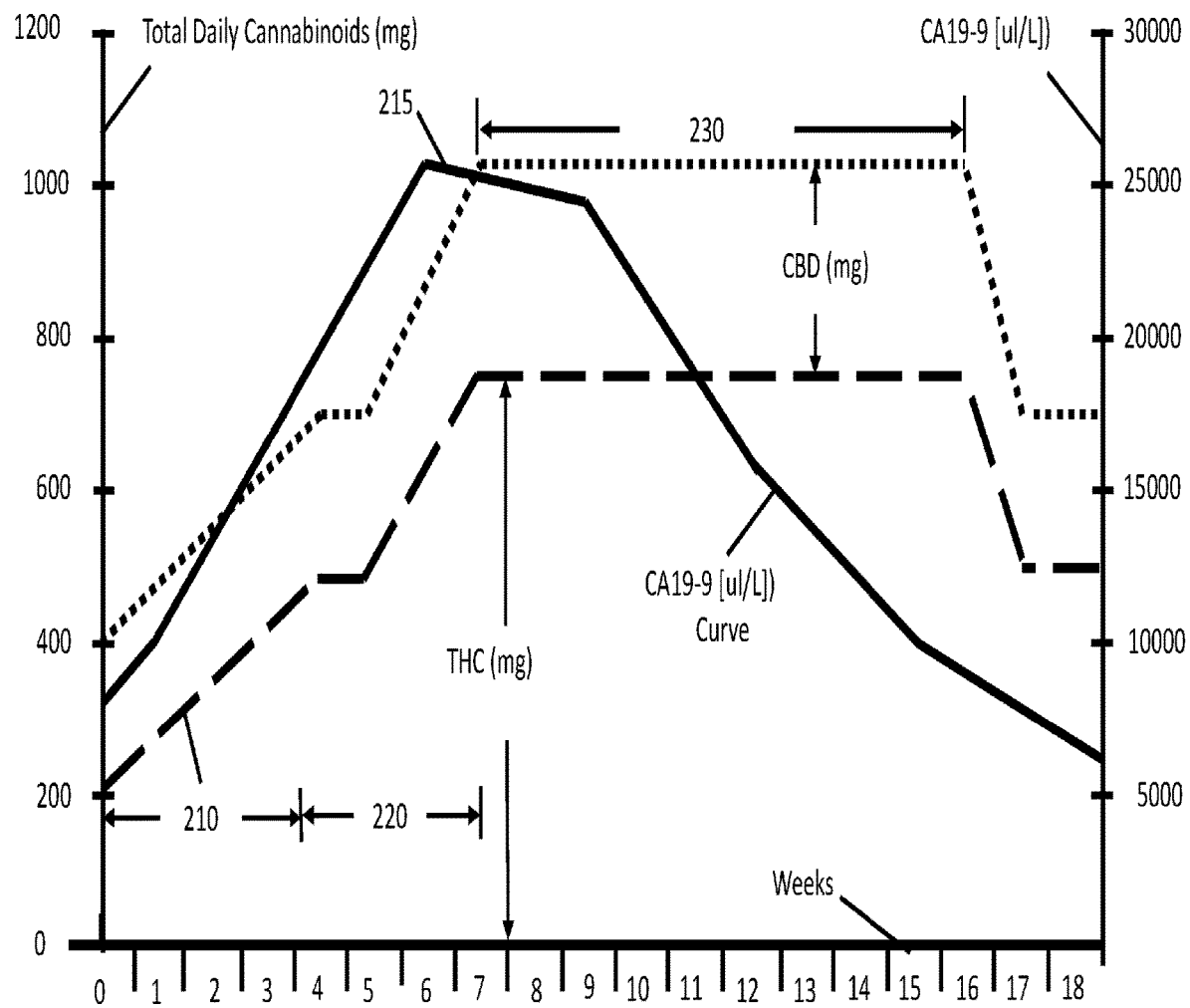
FIG. 2 illustrates the administration of varying amounts of THC and CBD over time and illustrates physiological factors measured when treating pancreatic cancer in human Patient-O.

The Applicant notes that both physiological effects and pathological factors were observed in a human patient suffering from stage 4 pancreatic cancer. The human patient, herein, referred to a "Patient-0" was treated according to the treatment methodology illustrated in FIG. 2. Patient-0 received varying amounts of THC and CBD over time and FIG. 2 illustrates physiological factors measured when treating pancreatic. The graph of FIG. 2 includes a first vertical axis of total daily cannabinoids in milligrams (mg), a second vertical axis of bio-marker CA19-9 measured in micro-liters per liter (ul/L), and a horizontal axis of time in weeks. Cannabinoid dosages, including THC and CBD, are started and increased over a first period of time 210. The curve shown with the large dashes shows a measure of THC being administered to the patient every day. The curve shown with the small dashed shows a measure of THC (mg) plus CBD (mg) being administered to the patient every day. Note that a measure of CBD being administered may be determined by subtracting the milligram (mg) dosage indicated by the small dashed curve minus the mg dosage shown by the large dashed curve. For example at time zero an initial total cannabinoid dosage of 400 mg/day was administered to the patient. Of that 400 mg/day, 200 mg was THC, so the mg/day dosage of CBD was 400 mg-200 mg=200 mg. Patient-0 received cannabinoid treatments in capsule form according to the graph of FIG. 2. Patient-0 also received 155 mg Gemcitabine in 250 milliliter (ml) saline solution on a schedule of two weeks on/one week off. After 7 days of cannabinoid treatment Patient-0 stopped presenting typical symptoms of cannabis used, such as red eyes, slurred speech, and clumsiness. After 10 day Patient-0 reported no longer feeling the euphoric effects of cannabinoid use (i.e. the patient no longer felt "high" or "stoned"). Patient-0, therefore, adapted to the cannabinoids because Patient-0 stopped exhibiting various physiological effects after 7 to 10 days on the cannabinoid treatment regimen.

Cannabinoid dosages were increased again in a second period of time 220 until levels of blood bio-marker C19-9 are observed reducing 215, then cannabinoid dosages are maintained over a third period of time 230 while the blood bio-marker C19-9 continues to reduce. Notice also that relative mg dosages of THC versus CBD may also be varied over time where an amount of THC versus CBD may be increased at a greater rate relative over time or visa-versa. FIG. 2 also shows cannabinoid dosages being reduced after the third period of time 230. The size of Patient-0's pancreatic tumors where also observed to reduce over the course of the treatment regimens administered to Patient-0.

Parametric data relating to the treatment of Patient-0 was presented in May 2014 to the American Association of Cancer Researchers at a special conference on pancreatic cancer in Louisiana. This data was also provided to members of the United States Congress when representatives of PanCan.org visited Washington D.C.

High doses of THC may cause cancer tumors to shrink by inducing the death of cancer cells by the mechanisms of autophagy and apoptosis. The cancer may be attacked by promoting the digestion of cellular constituents by enzymes of the same cell (autophagy), and also by accelerating a genetically determined process of cell self-destruction that may be marked by the fragmentation of nuclear DNA (apoptosis).

Since apoptosis may be activated either by the presence of a stimulus or by the removal of a stimulus or suppressing agent, different cannabinoid types may activate apoptosis in different types of cancer cells. The present invention may also include identifying a type of cancer by identifying its genome and by identifying whether the cancer includes specific types of cannabinoid receptors. This process may also include determining how many cannabinoid receptors are included in a cancer cell relative to the number of cannabinoid receptors that are included in a normal cell. Since Donadelli discovered forms of pancreatic cancer that have 100× more CB1 receptors than normal cells, and since THC bonds with the CB1 receptor, a patient consuming high levels of THC may saturate the pancreatic cancer cells with THC. The treatment regimen may also include administering combinations of THC, CBD and other cannabinoids for various reasons. For example, by administering CBD a patient should receive anxiety relief.

By administrating specific cannabinoids over a first period of time, a patient receives anxiety relief and is allowed to acclimate to cannabinoids while the cannabinoids begin interfering with metastatic processes that are related to the spread of cancer. Cannabinoid dosages may be increased in one or more steps over a period of time.

When administering cannabinoids the method for treating cancer may begin by observing a physiological response in a person after administrating one or more cannabinoid medications according to a first treatment dosage regimen. That regimen may include administering more specific types of cannabinoids over a first period of time in one or more discrete administrations. Physiological responses observed may include red eyes, slurred speech, forgetfulness, clumsiness, and lack of attention. Other physiological responses observed may include muscle relaxation, reduced sensitivity to pain, reduced swelling/inflammation, and increased mobility.

The method for treating cancer may also include administrating one or more different cannabinoid medications according to a second treatment dosage regime over a second period of time while monitoring one or more pathological factors. The one or more pathological factors monitored during the second period of time may include monitoring the size of a tumor or monitoring a bio-marker in the blood of a patient. When treating some forms of adenocarcinoma the monitored bio-marker may be C19-9. When a desirable pathological effect is observed a practitioner could conclude that the treatment regime is benefiting the patient. Alternatively both physiological effects and pathological factors may be observed during the first period of time until a desirable pathological effect is observed. After a desired pathological effect has been observed cannabinoid dosages may be maintained or be increased again while monitoring the pathological factors. When a physiological response is observed to abate after administering a cannabinoid, a practitioner may determine that the patient is adapting to the cannabinoids that they have been administered.

The method of the invention may also include administrating a third treatment cannabinoid dosage over a third period of time, and a fourth cannabinoid dosage over a fourth period of time. The cannabinoid dosage administrated over the fourth period of time may be a reduced dosage as compared to dosage administered over the third period of time. Successive periods of time may be necessary to achieve successful treatment outcomes.

A discussed above a cannabinoid regimen for treating cancer that has been adapted to humans may include increasing cannabinoid dosages over time and include a chemotherapy agent, a KRAS inhibitor, or both.

The present invention also includes a plurality of different formulations of cannabinoid medications that include different proportions/ratios or relative milligram dosages of different cannabinoids. The different formations may be provided in pill or capsule form. The formulations may also allow a practitioner to change dosages by administering, to the patient, a different pill or capsule from a plurality of different formulations. An exemplary table of different formulations consistent with the present invention is shown in table 1. The cannabinoid formulations of the present invention may be used to treat cancer or other ailments including, yet not limited to Parkinson's disease, epilepsy, or neuropathic pain. Table 1 includes low THC, balanced THC-CBD, and low CBD medication formulations. Note how the formulations scale in a series of steps that are similar to an exaggerated exponential. For example, an exponential scales [1, 2, 4, 8, 16] where entries in the table scale [1, 2, 5, 10, 20]. Other exemplary formulations include [2, 4, 10, 20, 40], [0.5, 1, 2, 5, 10], [50, 125, 250, 500, 1250], and [100, 200, 500, 1000, 2000].

Note that each of the formulations in table 1 include two different cannabinoids. While THC and CBD are illustrated, other cannabinoids may also be included in a formulation consistent with the present invention. Cannabigerol (CBG), for example, may be included in a formulation. By providing health practitioners with cannabinoid medications that scale, a practitioner may adjust dosages provided to a patient as desired. Also by providing two or more different cannabinoids a practitioner may select a formulation based on a treatment strategy. When treating epilepsy or spasticity disorders, a high CBD formulation may be selected. When treating forms of cancer with a high number of CB1 receptors, a high THC formulation may be selected. In other instances a balanced cannabinoid medication may be administered.

TABLE 1

Dosage levels of cannabinoids

| Low THC | | Balanced THC-CBD | | Low CBD | |
| --- | --- | --- | --- | --- | --- |
| 0.5 | 10 | 10 | 10 | 10 | 1 |
| 1 | 20 | 20 | 20 | 20 | 2 |
| 2 | 50 | 50 | 50 | 50 | 5 |
| 5 | 100 | 100 | 100 | 100 | 10 |
| 10 | 200 | 200 | 200 | 200 | 20 |
| THC mg | CBD mg | THC mg | CBD mg | THC mg | CBD mg |

The embodiment of the present invention that combines a cannabinoid treatment, chemotherapy, and a KRAS inhibitor may prove to be the most effective way to treat certain forms of cancer.

Figure 3:
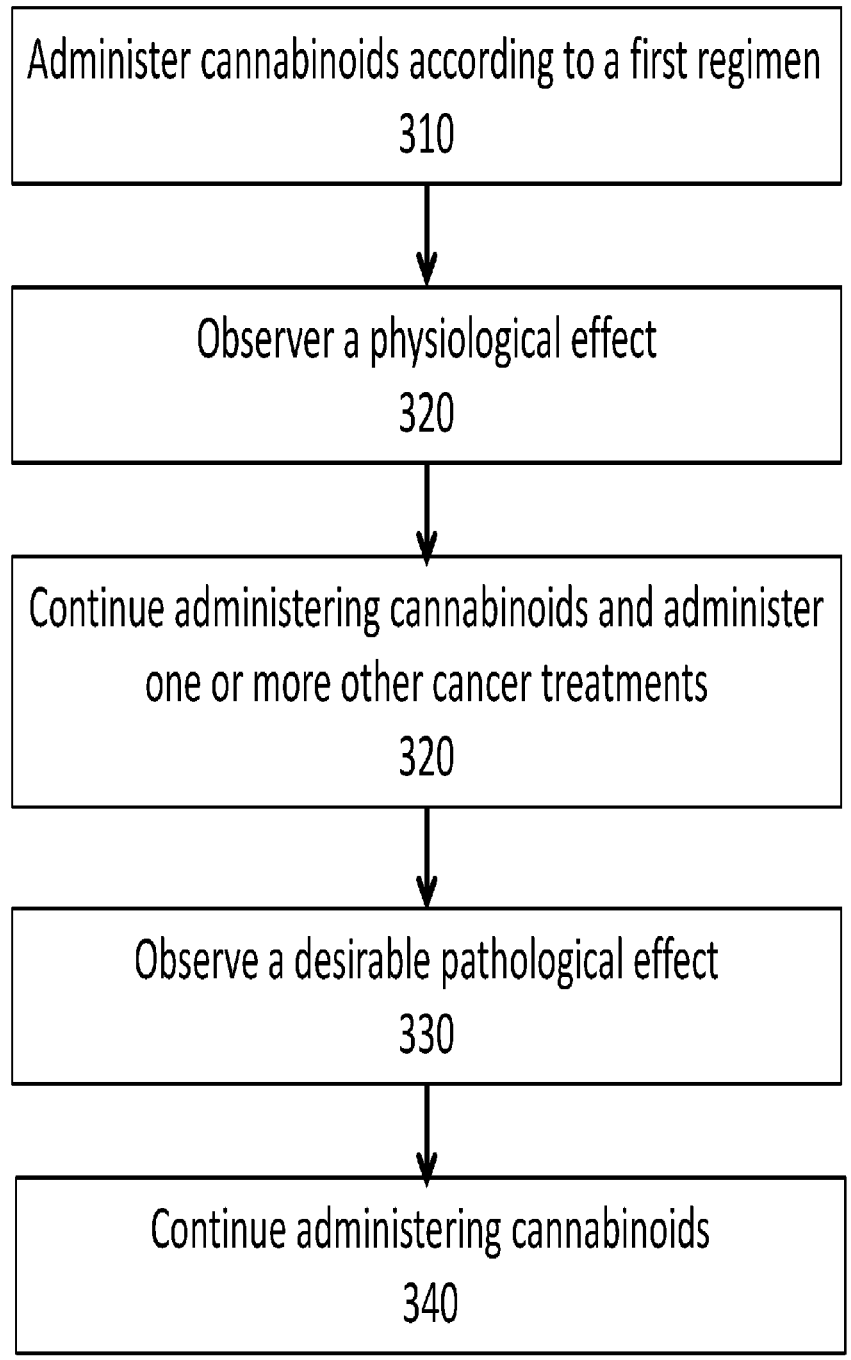
FIG. 3 illustrates an exemplary methodology consistent with the presently claimed invention.

FIG. 3 illustrates an exemplary methodology consistent with the presently claimed invention. In step 310 cannabinoids are administered according to a first treatment regimen. The first treatment regimen may include increasing mg dosages of cannabinoids over time. In step 320 a physiological effect of the person is observed. Next in step 320 the administration of cannabinoids may be continued and one or more other cancer treatment methods may be administered to the patient. Step 320 may also include increasing cannabinoid dosage levels administered to the patient on a daily basis. Then in step 330 a pathological effect may be observed. Finally in step 340 the administration of cannabinoids may be continued.

Note that the present invention may begin by administrating cannabinoids to a patient followed by administering a second cancer fighting methodology. The present invention may also begin by administering cannabinoids combined with one or more other methods for fighting cancer. When concerned with mitigating the effects of nausea induced by chemotherapy a chemotherapy treatment may be preceded by one or more cannabinoid treatments. Furthermore, cannabinoids may be administered after chemotherapy treatments or KRAS treatments have been terminated. The method may also include administering an immunotherapy agent that stimulates an increased immune response. Exemplary immunotherapy agents that may be administered include, yet are not limited to administering: an cytotoxic T-lymphocyte antigen 4 (CTLA-4) blocking treatment, an agent that affects the programmed cell death 1 receptor (PD-1) on T cells, a vaccine, a bacteria (dead or alive), or by administering an adoptive T cell transfer regimen. An adoptive T cell transfer regimen includes removing T cells are removed from a patient, expanding the T cells in a laboratory, and re-infusing the expanded T cells into the patient.

In certain instances an anti-CTLA-4 or an anti-PD-1 immunotherapy agent may be administered. Since anti-CTLA-4 antibodies such as ipilimumab have been associated with the side effect of excessive inflammation leading to increased rates of colitis, dermatitis, and hepatitis combining and anti-CTLA-4 agent with an anti-inflammatory cannabinoid treatment. The combining an anti-CTLA agent with cannabinoids the negative side effects of drugs like ipilimumab may be mitigated. As such an immunotherapy may be administered before, after, or coincident with administering a cannabinoid regimen to a patient.

The method may also include administering an immunotherapy agent that stimulates an increased immune response. Exemplary immunotherapy agents that may be administered include, yet are not limited to administering: an cytotoxic T-lymphocyte antigen 4 (CTLA-4) blocking treatment, an agent that affects the programmed cell death 1 receptor (PD-1) on T cells, a vaccine, a bacteria (dead or alive), or by administering an adoptive T cell transfer regimen. An adoptive T cell transfer regimen includes removing T cells are removed from a patient, expanding the T cells in a laboratory, and re-infusing the expanded T cells into the patient.

In certain instances an anti-CTLA-4 or an anti-PD-1 immunotherapy agent may be administered. Since anti-CTLA-4 antibodies such as ipilimumab have been associated with the side effect of excessive inflammation leading to increased rates of colitis, dermatitis, and hepatitis combining and anti-CTLA-4 agent with an anti-inflammatory cannabinoid treatment. The combining an anti-CTLA agent with cannabinoids the negative side effects of drugs like ipilimumab may be mitigated. As such an immunotherapy agent such as CTLA-4 may be administered before or after administering a cannabinoid regimen to a patient.

Cannabinoids can be administered to a patient before, in combination with, or after other one or more other therapies.

The present disclosure describes treatment regimens using different cannabinoid formulations. Treatment regimens of the present disclosure include treating cancer, treating side effects of chemotherapy (including nausea and appetite loss), treating post-traumatic stress disorder (PTSD), and Parkinson's rapid eye movement behavior sleep disorder (RBD).

When attempting to help individuals who potentially could benefit most by cannabinoid consumption under California's compassionate care act, cancer patients suffering from the side effects cancer treatment therapy/medication induced loss of appetite and nausea. Observations included increased appetite as typified by a patient ordering pizza as chemotherapy was being administered and reduced nausea. Dosages of 5 milligrams (mg) to 10 mg THC, and 5 mg-10 mg of CBD were identified as being effective in treating these side effects. These formulations were identified as being more effective than Marinol (a synthetic form of pure THC) or dronabinol (another substantially pure THC formulation). Observations indicate that patients consuming CBD with THC adapt to consuming the medications more reliably. This especially true when the patients have had little previous experience with consuming THC. Some new patients consuming THC quit consuming it because of the psychoactive side effects of THC. When CBD is combined with THC, patents adapt or gain tolerance to THC consumption or were more able to tolerate combined dosages of THC and CBD as compared to consuming THC alone. As such, the Applicant's presently claimed invention provides improvements over substantially pure medications such as Marinol or dronabinol. Side effects of Marinol of or dronabinol of feeling high, dizziness, confusion, anxiety, or somnolence may be mitigated by providing effective weights of CBD with THC. As such, medication formulations for treating the side effect of chemotherapy may begin with medicinal formulations (in capsules, for example) that include 2 to 2.5 mg of CBD and THC that can be consumed by a patient in one or more administrations in a day, where each administration may include consuming one or more medicinal formulations in an administration.

In a separate set of observations and tests, war veterans suffering from post-traumatic stress disorder (PTSD) were observed purchasing large amounts of un-tested hashish from local dispensaries on sale days. After observing this, samples of this hashish were tested. These test results revealed that the hashish included both THC and CBD, where THC dominated. Veterans suffering from PTSD received cannabinoid infused chocolates with controlled dosages. This process identified that chocolates infused with 44 mg of THC and 4 mg of CBD were effective in treating these veterans PTSD. Information reported by veterans identified that many of them were also suffering from pain and had been consuming opiates to combat the pain. The opiates that these veterans were taking reportedly exacerbated PTSD symptoms. What was also discovered was that administrations of THC alone, increased psychotic side effects associated with PTSD, as such THC alone is either not effective or provided limited benefits as a combed THC/CBD medication when treating pain combined with PTSD. Patients of Laguna Honda Hospital in California were also provided medications that included both THC and CBD and reported benefit.

As such, medication formulations for treating the PTSD may include 44 mg of THC and 4 mg of CBD, or may include milligram dosage of THC and CBD that evenly divide (or that approximately divide) into 44/4. For example, 10 mg THC and 1 mg CBD or 11 mg THC and 1 mg CBD that can be consumed by a patient in one or more administrations in a day, where each administration may include consuming one or more medicinal formulations in an administration.

Another separately studied treatment regimens using calibrated dosages of cannabinoids was for treating Parkinson's rapid eye movement (REM) sleep behavior disorder (RBD). 75% of patients in the study reported a reduction in RBD symptoms when using a daytime dose including 10 mg THC and 1 mg CBD (i.e. 50% THC and 50% CBD) combined with a night time dose including 1 mg THC and 10 mg CBD (9% THC and 91% CBD) where other cannabinoid ratio tested showed only minor reductions in RBD symptoms. A more detailed review of specific results related to this project are reviewed below and in an attachment provided with a supplement to this specification.

Symptoms of Parkinson's rapid eye movement sleep behavior (RBD) include patient's voluntary muscles not being paralyzed when in REM (rapid eye movement) sleep. In contrast, individuals that do not suffer from this ailment do not move when in REM sleep as their voluntary muscles go into a state of paralysis. In contrast, those that do suffer from this ailment move when in a dream state. One of the individuals that participated in this study reported that he was dreaming that he was fighting with an alligator and then he awoke choking his wife. Other patients and spouses of patients have reported punching, kicking, yelling, cursing, and laughing. Because of such issues individuals that suffer from RBD commonly sleep in different rooms than their significant others.

Initially, two of the participants in the study reported that they felt some improvement in their RBD symptoms when taking a cannabis oil obtained from a dispensary in California. One issue that occurs when patients consume cannabis oil is that they rarely consume consistent dosages twice. Another issue that apparently occurred with this study is that ratios of THC and CBD contained in the cannabis oil consumed by the initial two patients was incorrect, possibly flipped (i.e. transposed). This led to the belief that a medication high in CBD and low in THC might be effective in treating RBD. Because of this, the study began with a medication that included a high dosage of CBD) combined with a low dosage of THC mixed in a volume of fatty foodstuff. Before the patients consumed cannabinoids, the patient and their spouses collected data in Phase 0 of the study where the patients did not consume cannabinoids for two weeks. Next, in Phase 1 of the study, the patients consumed the manufactured medications (high in CBD and low in THC) at night before bed. Phase 1 tests, showed some improvement in arm and voice RBD symptoms as illustrated in the "Results by Arms, Legs, Voice" chart in the study summary provided with this response.

Next in Phase 2 of the study, a daytime dose was introduced that included increased amounts of THC. While Phase 2 was intended to use a 1/1 ratio of THC to CBD, verification tests indicated that Phase 2 really used a 0.9/1 THC/CBD ratio. The intent of the Phase 2 test was to see if tremors associated with Parkinson's disease could be reduced by the patients consuming an increased amount of THC during the day combined with the same high CBD formulation of Phase 1. Phase 3 used reformulated THC/CBD medications with a 1/1 ratio combined with the same high CBD formulation of Phase 1 and Phase 2.

As can be seen in the attached addendum to the specification: "The Santa Cruz Study of REM Sleep Behavior Disorder in Parkinson's Patients," specific cannabinoid formulations provided significant improvements in Phase 2 and Phase 3 of this study. More specifically, the "Results by Phase, Weighted Average Sleep Activity Scores" chart shows no improvement in Phase 1 and identical improvements in Phase 2 and Phase 3.

The "Results by Arms, Legs, Voice" chart for Phase 1 shows some improvement in arms and voice scores, yet some worsening in legs scores as compared to Phase 0. This chart also shows significant improvement in arms and voice scores for both Phase 2 and Phase 3, yet Phase 2 and Phase 3 scores for Legs were somewhat worse for than Phase 0. It appears that arms and voice RBD symptoms may be more responsive than leg RBD symptoms to cannabinoid therapy and that leg RBD symptoms are more persistent than arm and voice RBD symptoms.

The "Results by Patient, Average Sleep Score by Patient" shows some contrasting data by patient between Phase 0 and Phase 1, yet significant improvement in Phases 2 and 3 as compared to other phases in all but one instance.

Overall, the Parkinson's RBD sleep study indicates that both THC and CBD provide non-obvious benefits to patients, yet further study is required. The Applicant emphasizes that these results are not obvious and that they are related to patients consuming a mixture of different types of cannabinoids with different ratios. The Applicant notes that milligram dosages provided to patients included day time dosages 10 mg THC and 1 mg CBD (i.e. 50% THC and 50% CBD) combined with night time dosages including 1 mg THC and 10 mg CBD. These results have been "confidentially" provided to several member doctors of California's Society of Cannabis Clinicians (SCC).

As part of an experimental use to patients suffering from Parkinson's sleep behavior, patients holding valid California doctor recommendations were provided experimental cannabinoids mixed with a fatty foodstuff. Provided with this response is a summary paper entitled: "The Santa Cruz Study of REM sleep Behavior Disorder in Parkinson's Patients." This summary report details different ratios of cannabinoids consumed by patients at different times of the day. While some patients previously attempted to smoke cannabis or consume cannabis oil, these administrations suffered from limitations that include unknown cannabinoid dosage (cannabinoid weight in milligrams) and/or non-optimized absorption. The study included cannabinoid medications that included blends of ratios of THC and CBD mixed with a fatty foodstuff. In this experiment, patient spouses and patients reported best results in alleviating symptoms of RBD where a night time dose mendicants corresponded to a high amount of CBD as compared to THC and where a day time dose of corresponded to equal amounts of CBD and THC or a mendicant that included greater amounts of THC as compared to CBD. Note also that one patient stopped taking Clonazepam and another reduced Clozapine mendicants by 50%. Clonazepam and Clozapine are both medications associated with the treatment of Parkinson's symptoms.

The Applicant's work also includes formulations that may include two or more cannabinoids. In certain instances a formulation could include three cannabinoids where weights of one or more of those cannabinoids may scale according to at least an exponential (geometric) function in a series of steps. As such, a formulation could contain THC, CBD, and Cannabigerol (CBG) where CBG dosage scales (from formulation to formulation) more rapidly than weights of THC or CBD. For example, a weight of CBG or other cannabinoid may scale exponentially from capsule to capsule where weights of THC and CBD stay the same or scale linearly. In another example, weights of CBG and THC could scale exponentially from capsule to capsule as weights of CBD scales linearly.

While the Applicant has described capsules and suppositories in the present disclosure, cannabinoid formulations may also scale according to the present disclosure within preferred volumetric spaces. For example, within different sets of tinctures, in a liquid form, or in a form that liquefies when heated. As such, the Applicant's formulations may be in a capsule form, be a suppository, or be dispensed in a volume.

The Applicant's scaleable formulations allow the effects of cannabinoids to be studied by researchers, as different formulations may be administered to patients as effects of those cannabinoids are monitored. Here again, both physiological and pathological factors could be monitored by researchers over time by administering different formulations to an individual patient, to a group of patients, or to different groups (that may include a control group) of patients over time.

The Applicant's formulations may include two or more different cannabinoids of any of the hundreds of cannabinoids that exist in cannabis plants. The Applicant's formulations may also include controlling a weight of one or more terpenes. Cannabis plants are known to include various terpenes. For example, cannabis plants contain limonene, myrcene, and beta-caryophyllene among other terpenes. Levels of one or more terpenes included in a medication may be manipulated to take advantage of physiological effects attributed to or that might be attributed to these terpenes. Terpene levels can be manipulated when cannabinoid containing medicinal formulations are manufactured. This can facilitate the testing of effective levels of terpenes to include with specific weights/masses of cannabinoids when administered in a discrete formulation. The Applicant notes that different amounts of limonene may affect the absorption of cannabinoids, that different levels of myrcene may affect an amount of stimulation of cannabinoids on the medulla oblongata, and that different levels of beta caryophyllene may affect an amount of swelling (inflammation). Amounts of specific terpenes may be measured by weight or may be compared relative to weights of other terpenes in a formulation.

Cannabis plants include many different terpenes as well as cannabinoids that may be identified using gas chromatography, high pressure liquid chromatography, or by other means. Terpenes, such as limonene, myrcene, and beta caryophyllene are commercially available in the form of extracts derived from plant matter that is not cannabis. For example limonene may be derived from lemons, myrcene may be extracted from the thyme plant, and beta caryophyllene may be obtained from hops, rosemary, or cloves.

Testing of intermediate products or of raw plant matter can be used to identify profiles of essential elements contained within cannabis plant matter or within a cannabinoid containing intermediate product. In an example, a cannabis plant extract is tested, the testing identifying constituent components included in the plant extract. Typically such a plant extract may include one or more terpenes and one or more cannabinoids. Methods of the presently claimed invention may include adding terpenes derived from other plants besides cannabis to a plant extract when fabricating medications that include weights of one or more cannabinoids (such as 5 mg of THC and 50 mg of CBD in a capsule, for example). The testing may identify masses or weights of cannabinoids or terpenes included in a mass of an extract or in an identified volume of an extract. For example mass of cannabinoids and terpenes may be identified by testing one or more plant extracts via gas chromatography or high performance liquid chromatography.

In an example, the content of a cannabinoid containing intermediate product was identified to include masses of one or more specific cannabinoids and terpenes. For this example, the following assumptions are made: Testing indicates that a 1 ml volume of and cannabinoid containing intermediate product plant extract includes 200 mg THC, 20 mg CBD, and 0.3 mg myrcene. A target dosage of a formulation to fit into a 1 ml capsule is identified as including approximately 100 mg THC, 10 mg CBD, and 0.5 mg myrcene. Let us also assume that 1000 ml of this cannabis plant extract is available for incorporation into capsules and that a non-cannabinoid containing myrcene extract that includes 0.7 mg per ml is available.

Based on the assumptions above, 1000 ml of such an extract would contain 200,000 mg THC, 20,000 mg CBD, and 300 mg myrcene. Even though this is enough THC and CBD to produce 2000 capsules, each capsule would not include enough myrcene to meet the formulation requirement of 0.5 mg per capsule. Instead there is only enough myrcene in this extract to include only 300 mg/2000=0.15 mg of myrcene. The 1000 ml of extract requires an additional (0.5-0.3)*2000=400 mg of to meet the formulations myrcene requirement. Since each ml of the available myrcene extract includes 0.7 mg of myrcene the total number of ml of myrcene extract that needs to be added to the extract can be calculated: 200 mg=0.7 mg/ml*X: or X=(400 mg)/(0.7 mg/ml)=571 ml. After combining the 571 ml of myrcene extract with 1000 ml of extract, a resulting formulation would include a total volume of 1571 ml. Such a formulation could also be combined with other ingredients such that a total of 2000 ml of a formulation would be available for manufacturing 2000 of the 1 ml capsules. In such instances, a non-allergenic food grade oil or other substances could be added to the formulation. For example, 2000-1571=429 ml of grape seed oil could be added to the formulation.

The technique described above can be performed even when laboratory testing identifies a number of milligrams of CBD per gram of extract. The volumetric density of such an extract could be identified using the test results, a scale, and making volumetric measurements. For example, if such testing indicated that an extract included 80% THC by total weight and 100 g of such extract consumed a volume of 105 ml, then the 105 ml of extract would include 80 g of THC.

Similarly, two or more extracts could be combined by using test results, by making measurements, and by combining volumes those extracts to yield volumetric densities of cannabinoids when making medicinal formulations.

One or more cannabinoid containing intermediate products may be combined when creating medications according to formulas designed to identify densities of components included in a discrete formulation. Such formulations may include masses of specific cannabinoids in a volume of a discrete medication. For example, when 1000 capsules are fabricated, where each capsule should include 100 mg of THC, 10 mg CBD, and 0.05 mg of myrcene. Similarly, specific weights of limonene and/or beta-caryophyllene may be combined with one or more extracts when creating medicinal formulations.

One or more specific formulations may be tested with patients when various physiological and/or pathological effects of the medications are monitored. For example, blood levels of cannabinoids may be monitored when identifying effective weights of limonene to include in a formulation. In such an example, a level of THC may be monitored in a formulation that included 10 mg THC, 10 mg CBD, and different weights of limonene in different capsules. Since limonene may affect absorption rates, a patient consuming a cannabinoid formulation including more limonene may absorb cannabinoids more rapidly than the same patient consuming the same weights of cannabinoids, yet less limonene.

Weights of terpenes included in particular variations may include an desired weight, an identified weight, a predicted effective weight, or an identified effective weight. In certain instances, effective weights may correspond to weights that correspond to a physiological effect or effective identified weights may correspond to weights of terpenes that are associated with a measured pathological effect.

In another example, computerized axial tomography (CAT) scans or magneto-resonance image (MRI) scans of a patient's body may be taken after capsules including specific weights of cannabinoids, yet different weights of myrcene are consumed by a patient over time. A CAT scan or an MRI scan of a person's brain may be taken when observing how different levels of myrcene affect medulla oblongata or the blood brain barrier. Similarly, the effect of cannabinoid containing formulations including different weights of beta-caryophyllene may be monitored using CAT or MRI scans to quantify observed inflammation.

Other tests that may be performed when the Applicant's formulations are consumed, include, yet are not limited to eye examinations or monitoring the blood flow in the eyes or in other body parts. Effects of these medication's may be monitored through patient worn electronic devices, such as the type made by Fitbit, or swallowable devices made by Proteus Digital Health.

While this disclosure specifically references terpenes such as myrcene, beta-caryophyllene, and limonene, other terpenes be combined in a formulation. As such, the present disclosure identifies both formulations and the effects of cannabinoids when combined with specific weights of terpenes. In certain instances, terpenes added to cannabinoid containing intermediate products may include terpenes that are not typically found in cannabis plant matter.

Here again, physiological responses (effects) observed may include red eyes, slurred speech, forgetfulness, clumsiness, lack of attention, muscle relaxation, reduced sensitivity to pain, reduced swelling/inflammation, and increased mobility. Pathological effects may be effects measured using equipment, such as blood pressure machines, Fitbit, Proteus, CAT or MRI equipment, or blood chemistry test machines.

Once a desired terpene profile to include in a cannabinoid containing formulation is identified, medication may be fabricated to includes desired weights of specific cannabinoids and amounts of one or more specific terpenes. In an example, the desired terpene profile may include an amount of a terpene that should be included in a cannabinoid formulation. The formulation may be made from one or more cannabinoid containing intermediate products, where such cannabinoid containing intermediate products may be or include one or more plant extracts.

Alternatively effective weights of minerals or chemicals could be included in a formulation or be administered intravenously. For example, magnesium sulfate may be included in a formulation or administered intravenously when attempting to reduce the permeability of the blood brain barrier or to manipulating the medulla oblongata. As such, magnesium sulfate or other substances may be used to minimize transfer of cannabinoids into the brain.

The invention claimed is:

1. A method for treating adenocarcinoma by administering cannabinoids to a patient, the method comprising:
   administering a dosage of cannabidiol (CBD) and a dosage of tetrahydrocannabinol (THC) to the patient according to an adenocarcinoma treatment regimen that includes increasing the dosage of the THC administered to the patient over a first period of time to a second THC dosage associated with the adenocarcinoma treatment regimen;
   observing at least one physiological effect associated with the administration of the cannabinoids to the patient, the at least one physiological effect corresponding to one or more of red eyes, slurred speech, forgetfulness, clumsiness, and lack of attention of the patient;
   identifying that the patient is adapting to the administration of the cannabinoids based on a reduction of the one or more of the red eyes, the slurred speech, the forgetfulness, and the lack of attention of the patient;
   further increasing the dosage of the THC administered to the patient over a second period of time to a third THC dosage according to the adenocarcinoma treatment regimen;
   monitoring at least one of a tumor size or a blood bio-marker associated with the adenocarcinoma; and identifying that the at least one of the tumor size or the blood bio-marker of the cancer associated with the adenocarcinoma has reduced.

2. The method of claim 1, further comprising maintaining the administration of the increased third THC dosage over a third period of time, wherein:
a rate of increase of the THC dosage over the first period of time is less than the rate of increase of the THC dosage over the second period of time.

3. The method of claim 1, further comprising increasing the dosage of the CBD over the first period of time.

4. The method of claim 3, further comprising:
increasing the CBD dosage over the second period of time, wherein a rate of increase of the CBD dosage over the first period of time is greater than the rate of increase of the CBD dosage over the second period of time.

5. The method of claim 4, further comprising selecting a cannabinoid dosage level in milligrams of cannabinoids per kilogram body mass of the patient wherein at least one cannabinoid dosage administered to the patient is selected based on the kilogram body mass of the patient.

6. The method of claim 1, further comprising administrating a chemotherapy agent.

7. The method of claim 6, wherein the chemotherapy agent is an anti-metabolite.

8. The method of claim 6, further comprising administrating a KRAS inhibitor.

9. The method of claim 1 further comprising administering a KRAS inhibitor.

10. The method of claim 1, further comprising administering an effective dosage of one or more terpenes to the patient.

11. The method of claim 10, wherein the effective dosage of the one or more terpenes, the dosage of the CBD and the dosage of the THC are included in one or more pills.

12. The method of claim 10, wherein the one or more terpenes is myrcene.

13. The method of claim 10, wherein the one or more terpenes is lemonene.

14. The method of claim 10, wherein the one or more terpenes is beta caryophyllene.

15. The method of claim 10, wherein the one or more terpenes come from a plant other than cannabis.

16. The method of claim 1, further comprising decreasing the dosage of the THC administered to the patient over a fourth period of time.

17. The method of claim 1, wherein the THC dosage is increased on a daily basis over the first period of time and over the second period of time.

18. The method of claim 4, wherein the CBD dosage is increased on a daily basis over the first period of time.

19. The method of claim 18, wherein the CBD dosage is increased on a daily basis over the second period of time.

20. The method of claim 1, further comprising:
identifying that the patient no longer reports euphoric effects of cannabinoid consumption; and
identifying that the patient has adapted to the administration of the cannabinoids based on the patient no longer reporting the euphoric effects of the cannabinoid consumption.

* * * * *